US00PP24311P2

(12) United States Plant Patent

Klemm et al.

(10) Patent No.: US PP24,311 P2

(45) Date of Patent: Mar. 11, 2014

(54) *LOBELIA* PLANT NAMED 'KLELE12471'

(50) Latin Name: *Lobelia erinus*
Varietal Denomination: KLELE12471

(75) Inventors: Nils Klemm, Stuttgart (DE); Guido Von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 13/573,333

(22) Filed: Sep. 11, 2012

(51) Int. Cl.
*A01H 5/00* (2006.01)

(52) U.S. Cl.
USPC ..... Plt./451

(58) Field of Classification Search
USPC ..... Plt./451
See application file for complete search history.

*Primary Examiner* — Kent L Bell

(74) *Attorney, Agent, or Firm* — Jondle Plant Sciences Division of Swanson & Bratschun, L.L.C.

(57) ABSTRACT

A new and distinct *lobelia* plant named 'KLELE12471' particularly distinguished by being a compact variety with an upright to half-hanging habit and medium blue flowers with a distinct white eye, is disclosed.

1 Drawing Sheet

Genus and species: *Lobelia erinus.*
Variety denomination:
'KLELE12471'.

BACKGROUND OF THE NEW PLANT

The present invention comprises a new and distinct variety of *lobelia*, botanically known as *Lobelia erinus*, and hereinafter referred to by the variety name 'KLELE12471'. The new variety resulted from an open pollination conducted in June 2006 in Stuttgart, Germany, between female parent *lobelia* plant named 'LE 06 0141', (unpatented) and an unknown male parent *lobelia* plant. A single plant selection was subsequently chosen for further evaluation and asexual propagation.

The new variety was first propagated via vegetative cuttings and in vitro propagation in May 2007 in Stuttgart, Germany, and has been asexually reproduced repeatedly by vegetative cuttings for 15 generations. 'KLELE12471' has been found to retain its distinctive characteristics through successive asexual propagations via vegetative cuttings.

Plant Breeder's Rights for this variety have not been applied for. 'KLELE12471' has not been made publicly available more than one year prior to filing of this application.

SUMMARY OF THE INVENTION

The following are the most outstanding and distinguishing characteristics of this new variety when grown under normal horticultural practices in a glass greenhouse in Stuttgart, Germany.

1. Compact variety with upright to half-hanging habit; and
2. Medium blue flowers with a distinct white eye.

DESCRIPTION OF PHOTOGRAPH

This new *lobelia* plant is illustrated by the accompanying photograph which shows overall plant habit including blooms, buds, and foliage of the plant in full color. The colors shown are as true as can be reasonably obtained by conventional photographic procedures.

The photograph was taken in the spring of 2012 on a 3-month old *lobelia* plant grown in a 10 centimeter pot in a glass greenhouse in Stuttgart, Germany under normal horticultural practices.

DESCRIPTION OF THE NEW VARIETY

The following detailed descriptions set forth the distinctive characteristics of 'KLELE12471'. The data which define these characteristics were collected from asexual reproductions carried out in Stuttgart, Germany. The plant history was taken in the spring of 2012 on 3-month old plants grown in 10 centimeter pots in a glass greenhouse with a pinch date at week eight. This description is in accordance with UPOV terminology. Color designations, color descriptions, and other phenotypical descriptions may deviate from the stated values and descriptions depending upon variation in environmental, seasonal, climatic, and cultural conditions. Color readings were taken under natural light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:
- *Botanical.*—*Lobelia erinus.*
- *Common name.*—*Lobelia.*
- *Designation.*—'KLELE12471'.

Parentage:
- *Female parent.*—*Lobelia* plant named 'LE 06 0141' (unpatented).
- *Male parent.*—Unknown *lobelia* plant.

Growth:
- *Growth and branching habit.*—Upright to half-hanging.
- *Form.*—Rounded to flat.
- *Height* (*measured from the top of the soil, including any flowers*).—10.0 cm to 12.0 cm.
- *Width* (*horizontal plant diameter, including any flowers*).—10.0 cm to 12.0 cm.

*Time to produce a finished flowering plant.*—9 weeks.
*Outdoor plant performance.*—Very good.
*Time to initiate roots.*—After 2 weeks first root-tips visible, after 3 weeks rooted cutting, after 4 weeks saleable rooted cutting.
*Root description.*—Fine, white roots, freely branching and dense.

Leaves:
*Arrangement.*—Alternate.
*Length.*—2.0 cm to 2.5 cm.
*Width.*—0.4 cm.
*Shape.*—Elliptical to lanceolate, with upper leaves more lanceolate.
*Margin.*—Serrate.
*Apex.*—Obtuse.
*Base.*—Acute.
*Texture* (*both upper and lower surfaces*).—Smooth.
*Color* (*immature and mature leaves*).—Upper surface: RHS 137A. Lower surface: RHS 137C.
*Venation pattern.*—Pinnate. Venation color: RHS 137C.

Stems:
*Length.*—10.0 cm.
*Diameter.*—0.2 cm.
*Internode length.*—1.0 cm.
*Color.*—Between RHS 137A and RHS 141A.
*Texture.*—Smooth.
*Stem anthocyanin.*—Absent.
*Peduncle.*—Color: Between RHS 137A and RHS 141A. Length: 1.0 cm to 3.0 cm. Diameter: 0.05 cm. Texture: Smooth.

Flower buds:
*Color* (*when first opening*).—Greyish violet.
*Shape.*—Inverse drop.
*Length.*—0.8 cm.
*Diameter.*—0.25 cm.

Inflorescence:
*Blooming habit.*—Continuous.
*Lastingness of individual blooms on plant.*—Approximately 1 week.
*Fragrance.*—Absent.
*Inflorescence type.*—Raceme.
*Quantity of flowers and buds per flowering branch.*—10 to 15.

Flowers:
*Flower diameter* (*horizontal*).—1.5 cm.
*Flower height* (*vertical*).—1.0 cm.
*Immature flower.*—Upper lobe color: Upper surface: RHS 96B. Lower surface: RHS 96D. Lower lobe color: Upper surface: RHS 96B. Lower surface: RHS 96C.
*Mature flower.*—Upper lobe: Color: Upper surface: RHS 96B. Lower surface: RHS 96D. Length: 0.9 cm. Width: 0.6 cm. Shape: Obovate. Apex: Obtuse. Margin: Entire. Texture (both upper and lower surfaces): Smooth. Lower lobe: Color: Upper surface: RHS 96B. Lower surface: RHS 96C. Length: 0.6 cm. Width: 0.2 cm. Shape: Obovate. Apex: Obtuse. Margin: Entire. Texture (both upper and lower surfaces): Smooth.
*Corolla.*—Color inside: Pure white; closest to RHS NN155D. Color outside: Pure white; closest to RHS NN155D. Tube length: 1.0 cm. Diameter (at the top of the tube): 0.3 cm.
*Calyx.*—Quantity of sepals: 5. Color: Upper surface: RHS 137A (fused part) and slight RHS 141C anthocyanin coloration near margins. Lower surface: RHS 137A with slight anthocyanin coloration near margins about RHS 141C. Length: 1.0 cm. Fused part: 0.4 cm. Non-fused part: 0.6 cm. Diameter (at fusion point): 0.1 cm. Shape: Funnel, star-shaped with fused sepals in lower half. Apex: Acute. Texture (both upper and lower surfaces): Smooth.

Reproductive organs:
*Androecium.*—Quantity of anthers: 5. Filament length: 0.8 cm. Filament color: Bluish white. Pollen color: Grey. Pollen amount: Moderate.
*Gynoecium.*—Pistil length: 0.6 cm. Stigma color: Greyed violet. Style length: 0.7 cm. Style color: RHS 142B.

Fruit and seed set: None observed.
Disease and insect resistance: Typical of species.

COMPARISON WITH PARENTAL AND COMMERCIAL VARIETIES

'KLELE12471' differs from the female parent, 'LE 06 0141', (unpatented) in that 'KLELE12471' has a compact, upright to half-hanging habit with medium blue flowers, whereas 'LE 06 0141' has a vigorous, straight, upright habit with violet flowers.

'KLELE12471' differs from the commercial variety 'Techno Heat Upright Blue' (U.S. Plant Pat. No. PP19,056) in that 'KLELE12471' has green foliage, medium strong stems and smaller flowers, whereas 'Techno Heat Upright Blue' has grey foliage, stronger stems and larger flowers.

We claim:

1. A new and distinct *lobelia* plant named 'KLELE12471' as shown and described herein.

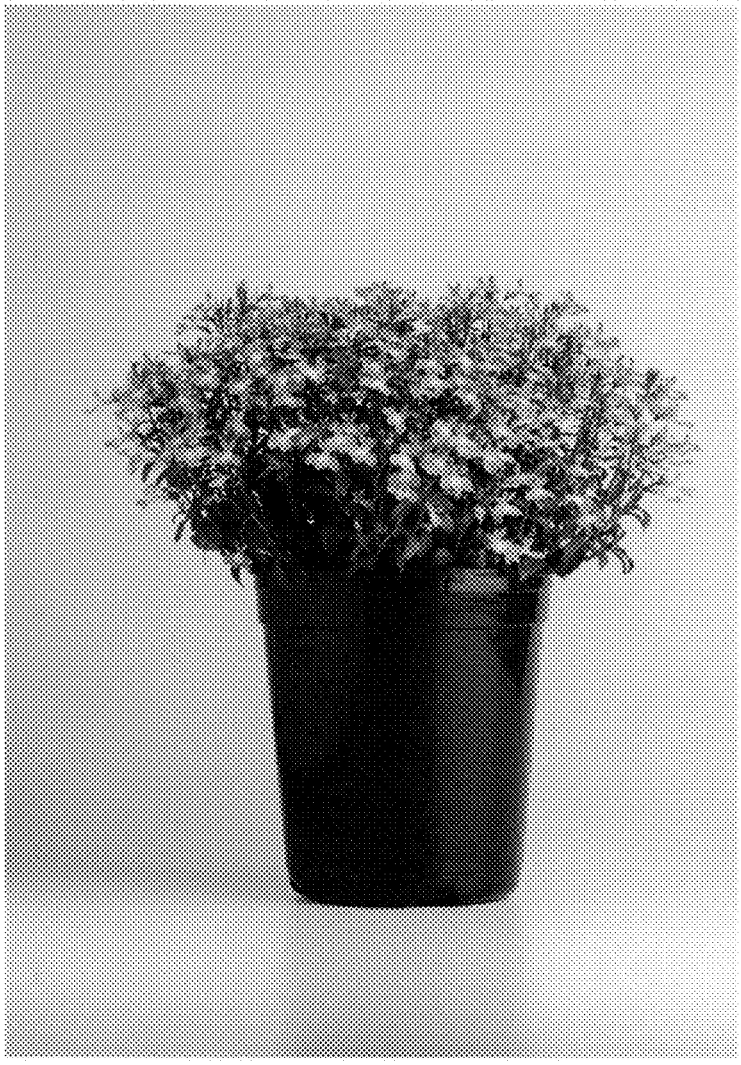

* * * * *